(12) United States Patent
Petasis

(10) Patent No.: US 6,602,817 B1
(45) Date of Patent: Aug. 5, 2003

(54) COMBINATION APPROACH TO CHIRAL REAGENTS OR CATALYSTS HAVING AMINE OR AMINO ALCOHOL LIGANDS

(75) Inventor: Nicos A. Petasis, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/425,498

(22) Filed: Oct. 22, 1999

Related U.S. Application Data
(60) Provisional application No. 60/105,489, filed on Oct. 23, 1998.

(51) Int. Cl.[7] .......................... B01J 31/00; B01J 27/24; B01J 21/02
(52) U.S. Cl. ..................... 502/172; 502/150; 502/167; 502/169; 502/170; 502/171; 502/200; 502/202
(58) Field of Search ................................ 502/104, 150, 502/151, 167, 172, 200, 169, 170, 171, 202

(56) References Cited

U.S. PATENT DOCUMENTS

| | | | | |
|---|---|---|---|---|
| 4,710,521 A | * | 12/1987 | Soukup et al. | 502/170 |
| 5,177,046 A | * | 1/1993 | Savoca et al. | 502/202 |
| 5,756,789 A | | 5/1998 | Bruce et al. | 556/14 |
| 6,030,917 A | | 2/2000 | Weinberg et al. | 502/104 |
| 6,069,109 A | * | 5/2000 | Kao et al. | 502/170 |
| 6,232,467 B1 | | 5/2001 | Petasis et al. | |

OTHER PUBLICATIONS

Laurent Deloux, "Asymmetric Boron–Catalyzed Reactions", Chem. Rev. vol. 93, pp 763–784, Apr. 1993.*

Nugent, William A., "Chiral Lewis Acid Catalysis. Enantioselective Addition of Azide to Meso Epoxides", Mar. 1992, *J. Am. Chem. Soc.*, vol. 114, No. 7, pp. 2768–2769.

R. Noyori, "Asymmetrical Catalysis in Organic Synthesis", *John Wiley & Sons, Inc.*, New York, New York, pp. 255–297 (1994).

Scope and Editorial Policy, *American Chemical Society*, Organometallics, vol. 21, No. 1, pp. 13A, 14A (2002).

* cited by examiner

*Primary Examiner*—Mark L. Bell
*Assistant Examiner*—J. Pasterczyk
(74) *Attorney, Agent, or Firm*—Fish & Richardson P.C.

(57) ABSTRACT

Functionalized amine derivatives are prepared by reacting an amine, a carbonyl derivative, and an organoboron compound under mild conditions. Organoboronic acids react with amines and alpha-hydroxy aldehydes to give anti-alpha-amino alcohols with very high diastereoselectivities (>99% de). When optically pure alpha-hydroxy aldehydes are used in this process, no racemization occurs and the products are obtained with very high enantioselectivities (>99% ee). The reaction also works with unprotected glyceraldehyde to give the corresponding amino diol derivatives, while unprotected carbohydrates give the corresponding amino polyols. The chiral amino alcohol products of this process or their derivatives, react further with metals or non-metals to give adducts that are effective catalysts for a variety of asymmetric reactions. Overall, the present invention relies on the facile synthesis of the chiral amino alcohol ligands for the rapid construction of combinatorial libraries of chiral catalysts. These libraries can then be used to identify the most suitable catalyst for a particular asymmetric transformation.

16 Claims, No Drawings

COMBINATION APPROACH TO CHIRAL REAGENTS OR CATALYSTS HAVING AMINE OR AMINO ALCOHOL LIGANDS

CROSS REFERENCE TO RELATED APPLICATIONS

This application is based on U.S. Provisional Application Serial No. 60/105,489, filed Oct. 23, 1998, incorporated herein by reference in full.

FIELD OF THE INVENTION

This invention relates to the fields of organic synthesis, asymmetric synthesis, catalysis, combinatorial catalysis, organoboron chemistry, combinatorial chemistry and medicinal chemistry. More specifically, the invention relates to methods for preparing chiral amine or amino alcohols used to prepare chiral reagents or catalysts which can be used for the synthesis of many other molecules.

BACKGROUND OF THE INVENTION

Although many chiral reagents or catalysts containing chiral amine or amino alcohol ligands and their methods of synthesis are known, these often have limited effectiveness giving products with high enantiomeric excess (%ee) only in certain cases. Most synthetic routes to chiral amines or amino alcohols proceed with low or mixed stereoselectivity, involve multiple steps, allow only limited types of substituents, or require highly reactive organometallics that involve cumbersome experimental conditions and necessitate additional protection-deprotection steps.

Rather than rely on the identification of a globally effective catalyst system, the present invention allows the facile construction of stereochemically pure amine or amino alcohol ligands that are subsequently used to form chiral reagents or catalysts. These can be prepared either individually or as combinatorial libraries and can be used to easily identify the most suitable catalyst for a given transformation.

A key feature of the present invention is the construction of amine or amino alcohol ligands in one or two steps and in high enantiomeric and diastereomeric purity.

SUMMARY OF THE INVENTION

This invention relates to a practical and effective method for the stereocontrolled synthesis of amines or amino alcohols for the preparation of a large variety of chiral catalysts for asymmetric synthesis. This process involves the one-step combination of certain organoboron derivatives, including organoboronic acids, organoboronates and organoborates with primary or secondary amines and certain carbonyl derivatives, such as α-keto acids, α-hydroxy aldehydes or carbohydrates. This process constitutes a three-component reaction and is suitable for the rapid generation of combinatorial libraries of amine or amino alcohols. These products can be converted to chiral reagents or catalysts via a subsequent reaction with an appropriate reagent, which can be present as a fourth component or can be used in a follow-up step.

The synthetic procedure is quite simple and works in a variety of solvents, including water, ethanol, dichloromethane and toluene. Product isolation is often very simple and can give fairly pure products without the need for chromatography or distillation. Of special significance is the fact that this process generates new C—C bonds with very high stereoselectivity (up to more than 99% de and 99% ee) when certain chiral components are used in the reaction. Due to its operational simplicity and the fact that no hazardous chemicals or special precautions are required, this invention is suitable for the practical and convenient synthesis of many types of amine or amino alcohol ligands, including stereochemically pure derivatives. These molecules can then serve as components of chiral reagents or catalysts which are useful for the synthesis of a variety of chiral organic molecules. In this manner, this invention is useful for the preparation of various chemicals, pharmaceuticals and agrochemicals.

DESCRIPTION OF THE PREFERRED EMBODIMENTS

Definitions:

An organoboron derivative, as defined herein, comprises a compound having a boron atom connected to at least one alkyl, allyl, alkenyl, aryl, allenyl or alkynyl group.

Alkyl groups of the present invention include straight-chained, branched and cyclic alkyl radicals containing up to about 20 carbons. Suitable alkyl groups may be saturated or unsaturated. Further, an alkyl may also be substituted one or more times on one or more carbons with substituents selected from the group consisting of C1–C6 alkyl, C3–C6 heterocycle, aryl, halo, hydroxy, amino, alkoxy and sulfonyl. Additionally, an alkyl group may contain up to 10 heteroatoms or heteroatom substituents. Suitable heteroatoms include nitrogen, oxygen, sulfur and phosphorous.

Aryl groups of the present invention include aryl radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

The term "combinatorial library" as used herein refers to a set of compounds that are made by the same process, by varying one or more of the reagents. Combinatorial libraries may be made as mixtures of compounds, or as individual pure compounds, generally depending on the methods used for identifying active compounds. Where the active compound may be easily identified and distinguished from other compounds present by physical and/or chemical characteristics, it may be preferred to provide the library as a large mixture of compounds. Large combinatorial libraries may also be prepared by massively parallel synthesis of individual compounds, in which case compounds are typically identified by their position within an array. Intermediate between these two strategies is "deconvolution", in which the library is prepared as a set of sub-pools, each having a known element and a random element. For example, using the process of the invention each sub-pool might be prepared from only a single amine (where each sub-pool contains a different amine), but a mixture of different carbonyl derivatives (or organoboron reagents). When a sub-pool is identified as having desired activity, it is resynthesized as a set of individual compounds (each compound having been present in the original active sub-pool), and tested again to identify the compounds responsible for the activity of the sub-pool.

The term "Metal" means any metal, metal derivative, or metal substitute useful for performing the a reaction in order to synthesize a reagant or catalyst. Examples include, but are not limited to B, Li, Mg, Al, Ti, V, Cr, Mn, Fe, Co, Ni, Cu, Zn, Zr, Mo, Ru, Rh, Pd, Ag, Re, Os, Ir, Pt, La, Ce and Yb.

General Description:

The first step of this invention involves a novel synthesis of a chiral amine or amino alcohol ligand and the second step involves the conversion of this amine or amino alcohol to a chiral reagent or catalyst.

The first step is based on the use of organoboron compounds in a C—C bond forming reaction where the electrophile is derived from a carbonyl and an amine and the product is a new substituted amine. There are many variations of this methodology involving different organoboron, carbonyl and amine components. For the purpose of illustration the following variations are described here.

Synthesis of Chiral Amines:

One aspect of the invention is a process for generating chiral amine derivatives of formula (1) or a combinatorial library of molecules of formula (1), by combining compounds (2), (3) and (4):

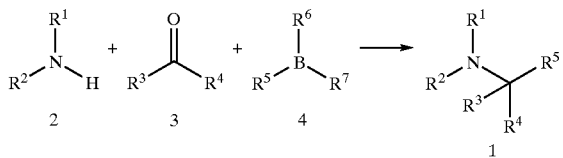

where $R^1$ and $R^2$ are each independently selected from the group consisting of alkyl, cycloalkyl, aryl, heteroaryl, acyl, carboxy, carboxamido, trialkylsilyl, aryldialkylsilyl, diarylalkylsilyl, triarylsilyl, phosphinyl, and —YR, where Y is selected from the group consisting of —O—, —$NR_a$—, —S—, —SO—, and —$SO_2$—, and R and $R_a$ are each independently selected from the group consisting of hydrogen, alkyl, aryl, heteroaryl, and acyl, or $R^1$ and $R^2$ together form a methylene bridge of 2 to 20 carbon atoms; and where $R^3$ and $R^4$ are each independently selected from the group consisting of hydrogen, hydroxy, alkoxy, aryloxy, heteroaryloxy, carboxy, amino, alkylamino, dialkylamino, acylamino, carboxamido, thio, alkylthio, arylthio, acylthio, alkyl, cycloalkyl; aryl, and heteroaryl; and where $R^5$ is selected from the group consisting of alkyl, cycloalkyl, aryl, heteroaryl, alkenyl, alkynyl and allenyl; $R^6$, $R^7$ are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, and heteroaryl, or together form a methylene bridge of 3 to 7 atoms.

Following their formation, compounds of formula (1) can be subsequently easily transformed to new derivatives. For example, removing groups $R^1$ and $R^2$ can provide primary amines, while joining two or more groups will result in the formation of cyclic or polycyclic amines.

The multicomponent nature of the process described in this invention allows the direct and rapid generation of combinatorial libraries of individual products or mixtures of products, by varying the desired substituents. Such libraries can be generated either in solution or in the solid phase, upon attachment of one substituent onto a solid support. For example, one may couple the amine component (2) to a substrate through either $R^1$ or $R^2$, and react the immobilized amine to a mixture of different organoboron compounds (3), where $R^5$ is a variety of different groups) and individual or mixed carbonyl compounds (4) to produce a mixture of bound products (1). Alternatively, the carbonyl compound may be immobilized, and a mixture of organoboron compounds and diverse amines added. Combinatorial libraries may be generated either as individual compounds or as mixtures of compounds.

In another embodiment of the invention an organoboron compound of formula (8) is combined with a preformed iminium derivative (5), aminol (6), or aminal (7), prepared by the combination of an amine (2) and a carbonyl compound (3), or by other methods:

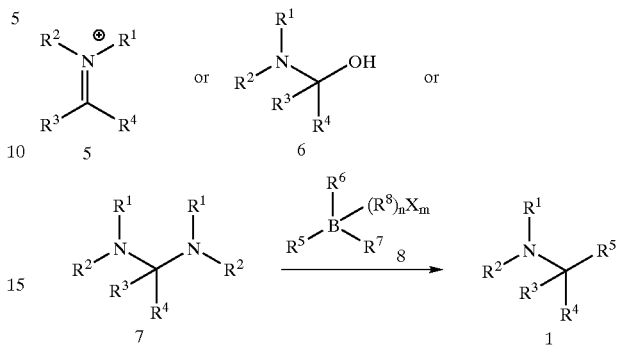

where $R^5$ is selected from the group consisting of alkyl, cycloalkyl, aryl, heteroaryl, alkenyl, alkynyl and allenyl; $R^6$, $R^7$ and $R^8$ are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, and heteroaryl, or together form a methylene bridge of 3 to 7 atoms; X is a positive counter ion, and n is 0 or 1. Such reactions can take place directly or upon the addition of a Lewis acid. In the case of fluoroborates (8) $R^6 = R^7 = R^8 = F$) the, reaction may be promoted by the addition of a silyl derivative $SiR^9R^{10}R^{11}R^{12}$, where $R^9$ is selected from the groups consisting of: chloro, bromo, iodo, alkoxy acyloxy, triflate, alkylsulfonate or arylsulfonate, while substituents $R^{10}$, $R^{11}$ and $R^{12}$ are selected from the groups consisting of: alkyl, cycloalkyl, aryl, alkoxy, aryloxy or chloro. A preferred $R^5$ is an alkenyl or aryl group leading to the formation of geometrically and isomerically pure allylamines or benzylamines (2), respectively.

Synthesis of Chiral α-Amino Carbonyl Derivatives:

This invention can be employed directly for the synthesis of chiral α-amino acids or other α-amino carbonyl derivatives (10) by combining an organoboron compound (4) with an amine (2) and an α-dicarbonyl compound (9).

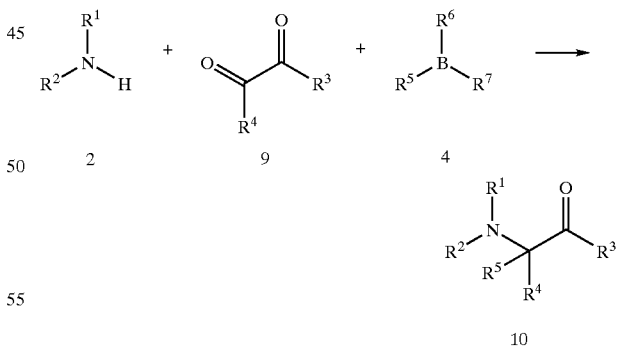

The reaction can proceed directly in a variety of solvents, including water, alcohols, ethers, hydrocarbons, chlorinated hydrocarbons and acetonitrile.

The stereochemistry of the product in these reactions can be controlled by the use of a chiral amine, a chiral carbonyl compound or a chiral organoboron derivative (L. Deloux et al., *Chem. Rev.* (1993) 93:763). The use of chiral amines or similar amino alcohol or amino acid derivatives can give products with a high degree of diastereocontrol (up to 99.5%de). Removal of the chiral group substituent can give the free amino acid with a high enantiomeric excess (up to 99.5%ee).

The types of organoboron compounds that can be used in this manner include compounds (4) that have $R^5$ selected from the group consisting of alkyl, allyl, cycloalkyl, aryl, heteroaryl, alkenyl, alkynyl and allenyl, including substituted and isomerically pure derivatives. The boron substituents $R^6$ and $R^7$ which do not appear in the product (10), are selected from the groups consisting of: hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, heteroaryl, including substituted and isomerically pure derivatives. Groups $R^6$ and $R^7$ may be connected together to form a bridge of 3 to 7 atoms. Substituents $R^3$ in compound (9) are selected from the group consisting of hydrogen, hydroxyl, alkoxy, amino, alkylamino, dialkylamino, hydroxyamino, alkyl, cycloalkyl, aryl, hetero aryl, including substituted and isomerically pure derivatives. Substituents $R^4$ in compound (9) are selected from the group consisting of hydrogen, carboxy, alkyl, cycloalkyl, aryl, hetero aryl, including substituted and isomerically pure derivatives. Substituents $R^1$ and $R^2$ in amine (2) are selected from the groups consisting of: alkyl, cycloalkyl, aryl, heteroaryl, hydroxy, alkoxy, aryloxy, heteroaryloxy, acyl, carboxy, amino, alkylamino, dialkylamino, acylamino, carboxamido, alkylthio, arylthio, acylthio, trialkylsilyl, aryldialkylsilyl, diarylalkylsilyl, triarylsilyl, phosphinyl, alkylsulfonyl or arylsulfonyl, including substituted and isomerically pure derivatives. Groups $R^1$ and $R^2$ may be connected together to form a bridge of 2 to 20 atoms.

The reactants are combined in approximately equimolar amounts in the solvent, and maintained at a temperature between about 0° C. and the reflux temperature of the solvent, preferably between about 25° C. and about 65° C., until the reaction is complete. The course of the reaction may be followed by any standard method, including thin-layer chromatography, GC and HPLC. In general, the reaction is conducted for about 1 to about 72 hours, preferably about 12 to about 24 hours. Product isolation usually gives fairly pure products without the need for chromatography or distillation.

The products (10) of the invention can be subsequently transformed to produce new derivatives. For example, if $R^3$ is hydroxyl, removing groups $R^1$ and $R^2$ can provide primary amino acids, while joining two or more groups will result in the formation of cyclic or polycyclic derivatives. A number of amine components (2) can be used which include $R^1$ and $R^2$ groups that can be easily removed in subsequent reactions. For example, benzylamine derivatives can be cleaved by hydrogenation, while others, such as the di(p-anisyl)methylamino group or the trityl group, can be removed under acidic conditions which prevent facile racemization.

The multicomponent nature of the process described in this invention allows the direct and rapid generation of combinatorial libraries of the products, by varying the desired substituents. Such libraries can be generated either in solution or in the solid phase, upon attachment of one substituent onto a solid support. In this case at least one of the groups $R^1$ through $R^7$ is a polymeric material. For example, one may couple an amine (2) to a substrate through either $R^1$ or $R^2$, and react the immobilized amine with a mixture of different organoboron compounds (4) (where $R^5$ is a variety of different groups) and individual or mixed dicarbonyl compounds (9) to produce bound products (10).

Alternatively, the dicarbonyl compound may be immobilized, and a mixture of organoboron compounds and diverse amines added. Combinatorial libraries may be generated either as individual compounds or as mixtures of compounds.

In order to improve the potential use of compounds (10) in the synthesis of chiral reagents or catalysts, additional steps may be carried out. For example, if compound (10) is an amino acid or amino ester ($R^3$=OH or OR) it can be converted to an amino alcohol of formula (11) by reduction. Alternatively, if $R^3$ in compound (10) is an amino group, reduction will lead to a diamine of formula (12).

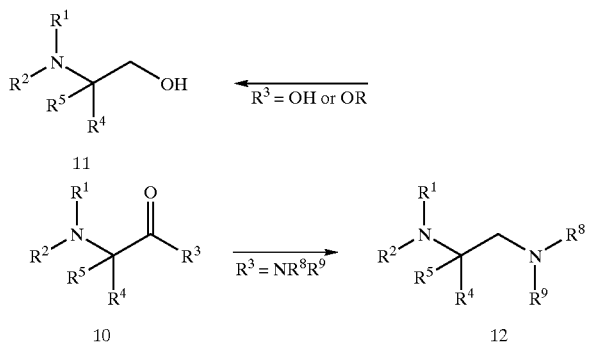

Synthesis of Chiral N-carboxymethyl Amino Acid Derivatives:

The use of α-amino acid derivatives (13) as the amine components in this process, can lead to N-carboxymethyl amino acid products (14) with a very high degree of diastereocontrol.

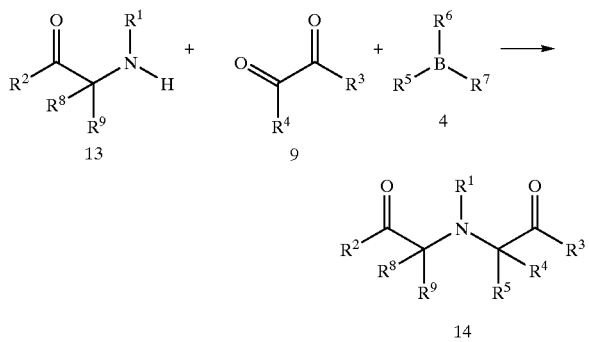

Substituents $R^1$ and $R^2$ in the amino acid component (13) are selected from the group consisting of alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^1$ and $R^2$ may also be connected to other amino acid units (peptides) or may be connected together to form a bridge of 2 to 20 atoms. Groups $R^8$ and $R^9$ are selected from the group consisting of alkyl, cycloalkyl, aryl, heteroaryl, acyl and carboxy,including substituted and isomerically pure derivatives. Groups $R^8$ and $R^9$ may be connected together or with other groups in (13), (9), or (4) to form a bridge of 3 to 7 atoms. Substituents $R^3$ and $R^4$ in compound (9) are each independently selected from the group consisting of hydrogen, hydroxy, alkoxy, aryloxy, heteroaryloxy, carboxy, amino, alkylamino, dialkylamino, acylamino, carboxamido, thio, alkylthio, arylthio, acylthio, alkyl, cycloalkyl, aryl, and heteroaryl. The boron substitutent $R^5$ in (4) is selected from the group consisting of alkyl, cycloalkyl, aryl, heteroaryl, alkenyl, alkynyl and allenyl. The boron substituents $R^6$ and $R^7$ which do not appear in the products, are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl and heteroaryl, including substituted and isomerically pure derivatives.

In order to improve the potential use of compounds (14) in the synthesis of chiral reagents or catalysts, additional steps may be carried out. For example, different variations of compound (14) can be converted to an amino diol of formula (15), a diamine alcohol of formula (16) or a triamine of formula (17).

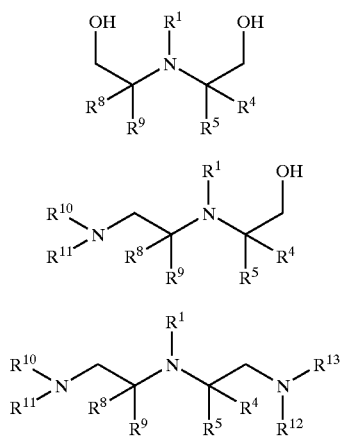

Synthesis of Chiral 1,2-Diamines and 1,2-Amino Alcohols:

In another embodiment of the invention an amine (2) and an organoboron compound are reacted with carbonyl derivatives of the general formula (18) to give products (19).

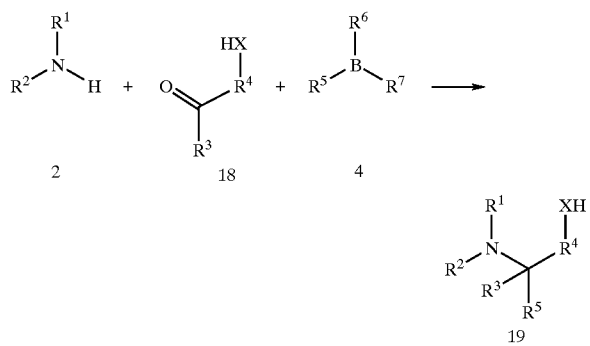

Groups $R^1$ and $R^2$ in the amine component (2) are selected from the groups consisting of: alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl or arylsulfonyl, including substituted and isomerically pure derivatives. Groups $R^1$ and $R^2$ may be connected together to form a bridge of 2 to 20 atoms. Groups $R^3$ in compound (18) are selected from the group consisting of hydrogen, alkyl, cycloalkyl, aryl, and heteroaryl. Groups $R^3$ in compound (18) have at, least one carbon atom and are attached to a group XH, where X is selected from a group consisting of —O—, —NR$_a$—, —S—, and R$_a$ is independently selected from the group consisting of hydrogen, alkyl, aryl, heteroaryl, acyl, hydroxy, alkoxy, aryloxy, heteroaryloxy, amino, alkylamino, dialkylamino, and acylamino. The boron substitutent $R^5$ in compound (4) is selected from the group consisting of alkyl, cycloalkyl, aryl, heteroaryl, alkenyl, alkynyl and allenyl. The boron substituents $R^6$ and $R^7$ which do not appear in the products, are selected from the groups consisting of: hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, heteroaryl, including substituted and isomerically pure derivatives. Groups $R^6$ and $R^7$ may be connected together to form a bridge of 3 to 7 atoms.

In one embodiment of the invention an amine (2) and an organoboron compound (4) are reacted with α-amino carbonyl derivatives (20) to give directly 1,2-diamines (21).

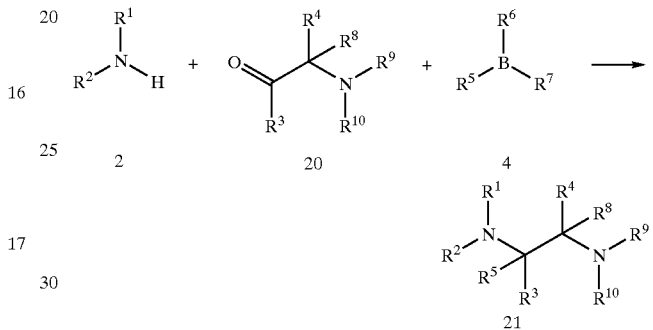

Groups $R^1$ and $R^2$ in the amine component (2) are selected from the groups consisting of: alkyl, cycloalkyl, aryl, hetero aryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl or arylsulfonyl, including substituted and isomerically pure derivatives. Groups $R^1$ and $R^2$ may be connected together to form a bridge of 2 to 20 atoms. Groups $R^3$, $R^4$ and $R^8$ in compound (20) are selected from the group consisting of hydrogen, alkyl, cycloalkyl, aryl, and heteroaryl. Groups $R^9$ and $R^{10}$ in compound (20) are selected from the group consisting of alkyl, cycloalkyl, aryl, heteroaryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^9$ and $R^{10}$ may be connected with other groups in compounds (2), (20) or (4) to form a bridge of 2 to 20 atoms. The boron substitutent $R^5$ in compound (4) is selected from the group consisting of alkyl, cycloalkyl, aryl, heteroaryl, alkenyl, alkynyl and allenyl. The boron substituents $R^6$ and $R^7$ which do not appear in the products, are selected from the group consisting of hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl and heteroaryl, including substituted and isomerically pure derivatives. Groups $R^6$ and $R^7$ may be connected together to form a bridge of 3 to 7 atoms.

The products (21) of the invention can be subsequently transformed to produce new derivatives. For example, removing groups $R^1$ and $R^2$ can provide primary amines, while joining two or more groups will result in the formation of cyclic or polycyclic derivatives. A number of amine components (2) can be used which include $R^1$ and $R^2$ groups that can be easily removed in subsequent reactions. For example, benzylamine derivatives can be cleaved by hydrogenation, while others, such as the di(p-anisyl) methylamino group or the trityl group, can be removed under acidic conditions which prevent facile racemization.

In another embodiment of the invention an amine (2) and an organoboron compound are reacted with an α-hydroxy carbonyl derivative (22) to give 1,2-amino alcohols (23). Compounds (22) can also exist in a hemiacetal form, and can include carbohydrate derivatives. The use of chiral derivatives (22) can form products (23) with a very high degree of diastereocontrol (up to greater than 99.5%de) and enantiocontrol diastereocontrol (up to greater than 99.5%ee).

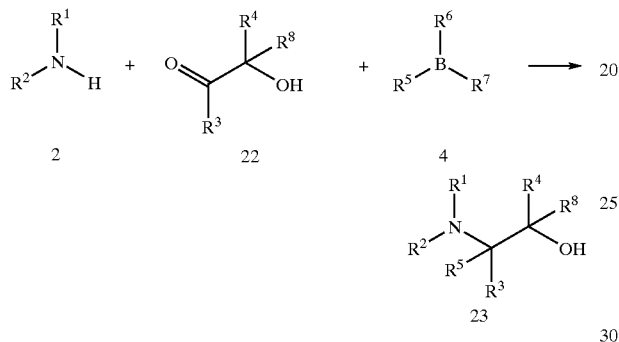

Groups $R^1$ and $R^2$ in the amine component (2) are selected from the group consisting of alkyl, cycloalkyl, aryl, heteroaryl, hydroxy, alkoxy, aryloxy, heteroaryloxy, acyl, carboxy, amino, alkylamino, dialkylamino, acylamino, carboxamido, alkyl thio, arylthio, acylthio, trialkylsilyl, aryldialkylsilyl, diarylalkylsilyl, triarylsilyl, phosphinyl, alkylsulfonyl and arylsulfonyl, including substituted and isomerically pure derivatives. Groups $R^1$ and $R^2$ may be connected with other groups in compounds (2), (22) or (4) to form a bridge of 2 to 20 atoms. Groups $R^3$, $R^4$ and $R^8$ in compound (22) are selected from the group consisting of hydrogen, alkyl, cycloalkyl, aryl, and heteroaryl. The boron substitutent $R^5$ in compound (4) is selected from the group consisting of alkyl, cycloalkyl, aryl, heteroaryl, alkenyl, alkynyl and allenyl. The boron substituents $R^6$ and $R^7$ which do not appear in the products, are selected from the groups consisting of: hydroxy, alkoxy, aryloxy, heteroaryloxy, chloro, bromo, fluoro, iodo, carboxy, amino, alkylamino, dialkylamino, acylamino, carboxamido, thio, alkylthio, arylthio, acylthio, alkyl, cycloalkyl, aryl, heteroaryl, including substituted and isomerically pure derivatives. Groups $R^6$ and $R^7$ may be connected together to form a bridge of 3 to 7 atoms.

An important feature of this variation is that when optically pure alpha-hydroxy carbonyl compounds (22) are used, no racemization occurs and the products (23) can be obtained as single enantiomers, with greater than 99% ee.

The products (23) of the invention can be subsequently transformed to produce new derivatives. For example, removing groups $R^1$ and $R^2$ can provide primary amines, while joining two or more groups will result in the formation of cyclic or polycyclic derivatives. A number of amine components (2) can be used which include $R^1$ and $R^2$ groups that can be easily removed in subsequent reactions. For example, benzylamine derivatives can be cleaved by hydrogenation, while others, such as the di(p-anisyl) methylamino group or the trityl group, can be removed under acidic conditions which prevent facile racemization. Also, the use of groups $R^5$ in the organoboron component, such as alkenyl or activated aryl or heteroaryl, followed by oxidative cleavage gives new products where the $R^5$ is a carbonyl group (aldehyde, ketone or carboxylic acid). Alternatively, the use of carbonyl components (22) having a group $R^4$ or $R^8$ consisting of a carbon atom attached to a hydroxyl group, as with many carbohydrate derivatives, followed by oxidative diol cleavage can produce new variations of compounds of the general formula (10).

Synthesis of Chiral Reagents or Catalysts:

The second step of this invention involves the reaction of a ligand derived from the first step, for example a compound of formula (1), (10), (11), (12), (14), (15), (16), (17), (19), (21), or (23) with a compound (24) of the general formula M(L)n to give a new chiral reagent or catalyst that contains one or more bonds among M and a heteroatom of the ligand.

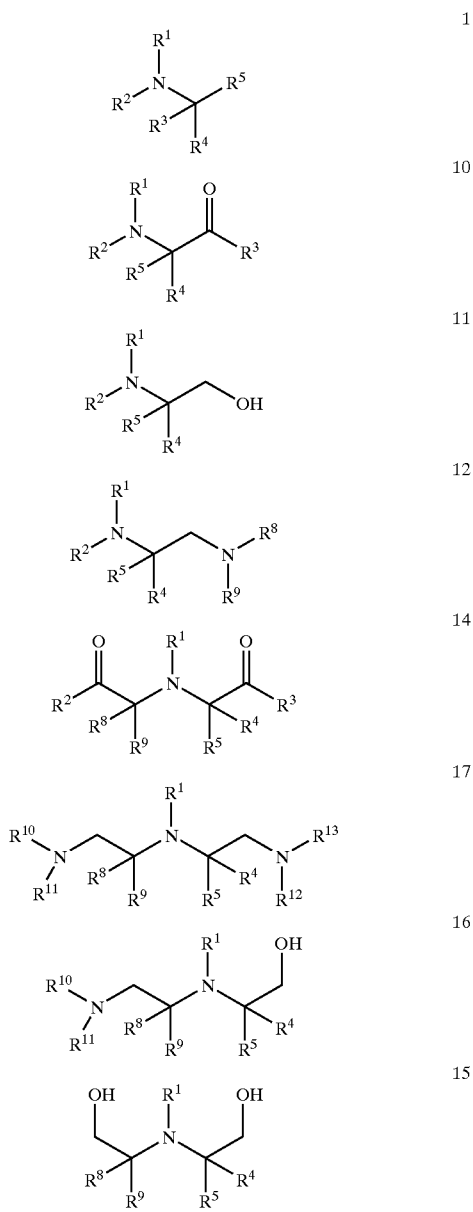

-continued

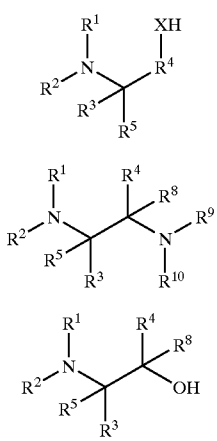

The atom M in formula (24) is selected from a group consisting of Li, Mg, B, Al, Ti, V, Cr, Mn, Fe, Co, Ni, Cu, Zn, Zr, Mo, Ru, Rh, Pd, Ag, Re, Os, Ir, Pt, La, Ce, Yb; where L is a ligand selected from a group consisting of chloro, bromo, iodo, fluoro, oxo, hydroxy, hydroperoxy, alkoxy, aryloxy, acyloxy, acetoacetyl, carboxy, nitro, amino, alkylamino, dialkylamino, azido, carbonyl, alkyl, alkenyl, dienyl, aryl, triflate, arylsulfonyl; where n is a number selected from 0–6; and where all ligands L are the same or different. Typical reagents of formula (24) include, but are not limited to: $ZnBr_2$, $Ti(OR_4)$, $Zr(OR)_4$, $YbCl_3$, $CrCl_2$, $WOCl_4$, $FeCl_2$, $RuCl_2$, $CoCl_2$, $NiCl_2$, $PdCl_2$, $CuCl_2$, $ZnCl_2$, AgOTf, $BCl_3$, $AlCl_3$, etc.

The chiral reagents or catalysts derived during the second step of this invention can be used in a large number of synthetic processes for the preparation of a large variety chiral products. These include: alkylations, aldol reactions, additions of nucleophiles to aldehydes or ketones, additions of nucleophiles to imine derivatives, Diels-Alder reactions, cycloadditions, cyclopropanations, aziridinations, carbonyl reductions, alkene hydrogenations, epoxidations, epoxide opening, etc.

Combinatorial Catalysis:

The facile synthesis of chiral ligands and chiral catalysts with this invention, allows the rapid preparation of large numbers of variants in the form of combinatorial libraries of catalysts. Such libraries can then be used to identify the optimum catalyst for any particular synthetic transformation. Following the screening of the library of catalysts, the most effective one can be easily prepared in large quantities for scale-up.

Solid Phase Variations:

When one of the three components (organoboronic acid, amine, carbonyl) is attached to a solid support, the resulting catalysts will also be attached to the solid support. This variation allows the preparation of even larger libraries via the usual pool and split approach.

Advantages and Improvements Over Existing Technology

Although there are many known methods for the synthesis of amine derivatives, due to the vital importance of these compounds and the many shortcomings of existing methods, any conceptually new and practical method in this are is of special significance. The present method offers a number of advantages over existing methods: Thus, this method is exceptionally environmentally friendly and practical. The reactions can be done in water or aqueous solvents at ambient temperature without using any toxic, hazardous or corrosive materials, such as cyanides, isonitriles, strong acids, strong bases, organotin, organocopper or other highly reactive organometallic compounds. Also, the reaction does not require an inert atmosphere, and can be done in the air. The present method also involves a smaller number of synthetic steps than most existing methods. All starting materials used in this type of reaction are either commercially available or can be readily prepared from commercially available reagents by a one-step procedure.

The use of organoboron compounds, particularly boronic acids and boronates, as nucleophilic components for amino acid and amine synthesis is a new concept which offers a number of distinct features, including the following:

1. Organoboronic acids are often crystalline, easy to prepare and easy to handle compounds that are stable in air and water. They are also non toxic and non hazardous. Although the synthesis and reactivity of these molecules has been studied extensively, the present method is the first successful example of their utilization in the synthesis of amines and amino acids.
2. The present method is highly versatile, allowing a high degree of structural variation in all of the reacting components. The process is also a multi-component reaction, allowing the one-pot construction of amine derivatives from several readily available building blocks. For these reasons, this method is easily applicable to the solid or liquid phase combinatorial synthesis.
3. The stereochemical control of the reaction can be accomplished not only with the use of chiral amine and carbonyl components but also with chiral organoboron derivatives. An advantage of boron-based auxiliaries is that they can be easily introduced and can be efficiently recycled after the reaction, thus making this method especially attractive for large scale applications.
4. Due to the facile synthesis of alkenyl and aryl boron derivatives, which proceed with complete control of geometry or positional isomerism, the present method is uniquely capable of furnishing isomerically pure products of this type.
5. Of special significance is the ability to directly use free amino acids in this reaction to give products of high stereochemical purity.

Although amines and amino alcohols are common ligands for many chiral catalysts, the processes described herein offer numerous advantages including:

1. Most of the existing methods cannot be adapted in a combinatorial approach to catalyst optimization, due to the required multi-step syntheses. While a number of combinatorial approaches to catalyst development were reported, all of these involve more elaborate sequential syntheses or chiral building-block combinations.
2. The present invention, involving a one-step stereocontrolled synthesis of amino alcohols from readily available starting materials, opens the way for the development of a practical combinatorial catalyst synthesis involving these well-established ligands.
3. The fact that the present invention allows the incorporation of multiple hydroxyl groups and other functionalities without any extra protection—deprotection steps facilitates the synthesis of some really complex chiral catalysts, that may be effective, even though their structures may be difficult to establish.
4. Because aldehyde racemization does not occur under the reaction conditions, relatively enantiomerically pure amino alcohols can be obtained by using enantiomerically pure alpha-hydroxy aldehydes, allowing for greater ease of recovery of the desired product.

5. By having one of the three components (organoboronic acid, amine, carbonyl) attached to a solid support prior to the reaction, the resulting catalysts will also be attached to the support, in a single reaction step. This allows for potentially faster screening of the compounds.
6. The invention allows the preparation of potentially large libraries of chiral catalysts with novel structures that may be used to identify the most effective system for a particular asymmetric transformation.

EXAMPLES

The following examples are put forth so as to provide those of ordinary skill in the art with a complete disclosure and description of how the processes of the present invention can be performed, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

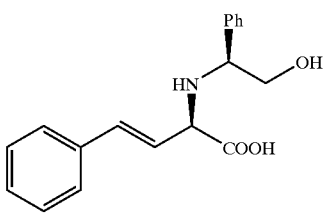

To a stirred solution of glyoxylic acid monohydrate (291 mg, 3.163 mmol) in dichloromethane (14 mL) was added (S)-(−)-2-phenylglycinol (434 mg, 3.163 mmol) in one portion. After 5 min (E)-2-phenylethenyl boronic acid (469 mg, 3.169 mmol) was added, and the reaction mixture was stirred vigorously at room temperature for 12 hours. The precipitate was isolated by filtration, washed with cold dichloromethane (15 mL) and acetone (10 mL) and dried under vacuum to give the expected adduct (733 mg, 78% yield, >99%de, >99%ee). $^1$H-NMR (360 MHz, $d_6$-DMSO) δ 7.2–7.5 (m, 10H), 6.54 (d, J=15.2 Hz, 1H), 6.20 (dd, J=15.2 Hz, 7.3 Hz, 1H), 3.84 (m, 1H), 3.64 (d, J=7.3 Hz, 1H), 3.45 (d, J=7.1 Hz, 2H). $^{13}$C-NMR (90 MHz, $d_6$-DMSO) δ 172.83, 139.79, 136.23, 131.07, 128.62, 128.34, 127.68, 127.51, 126.95, 126.38, 126.25, 65.97, 63.02, 60.96. HRMS-CI (M$^+$+1) calcd 298.1365, obsd 298.1449. Anal. Calcd for $C_{18}H_{19}NO_3$: C, 72.71; H, 6.44; N, 4.71. Found: C, 72.27; H, 6.41; N, 4.69.

Example 2

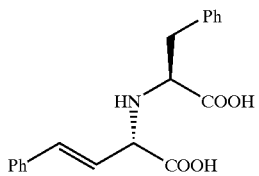

A mixture of L-phenylalanine (100 mg, 0.606 mmol), glyoxylic acid monohydrate (56 mg, 0.608 mmol) and (E)-2-phenylethenyl boronic acid (89 mg, 0.601 mmol) in methanol (8 mL) was stirred vigorously for 24 hours. The precipitate was isolated by filtration, washed with methanol (10 mL) and dried under vacuum to give (E)-2-[(S)-N-(1'-carboxy-2'phenyl)-amino-4-phenyl-3-butenoic acid (160 mg, 82% yield, 99%de, 99%ee). $^1$H NMR (360 MHz, DMSO-$d_6$) δ 7.18–7.45 (m, 10H), 6.58 (d, J=16.0 Hz, 1H), 6.10 (dd, J=16.0 Hz, 8.1 Hz, 1H), 3.91 (d, J=7.8 Hz, 1H), 3.45 (t, J=6.4 Hz, 1H), 2.88 (m, 2H). $^{13}$C NMR (90 MHz, DMSO-$d_6$) δ 174.9, 172.9, 138.0, 137.8, 136.1, 132.6, 129.4, 128.6, 127.7, 126.8, 126.4, 126.3, 61.7, 61.0, 59.6.

Example 3

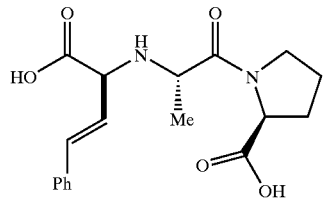

Alanine-proline (1,000 mg, 5.37 mmol), glyoxylic acid monohydrate (544 mg, 5.91 mml) and 2-phenylethenyl boronic acid (1,192 mg, 8 mmol) were vigorously stirred together in water (7 mL) for 48 hours. The precipitate was filtered, washed with acetone (2×10 mL) and dried to give a single crystalline product (1,488 mg, 80% yield, >99% de, >99%e) the structure of which was confirmed with X-ray crystallography. $^1$H NMR (360 MHz, DCl/$D_2$O) δ 7.10–7.25 (br, 5H), 6.92 (d, J=15.6 Hz, 1H), 5.78 (dd, J=15.6 Hz, 9.8 Hz, 1H), 4.75 (d, J=9.8 Hz, 1H), 4.15 (q, J=6.8 Hz, 1H), 3.84 (m, 1H), 3.20 (m, 2H), 1.58 (m, 2H), 1.41 (d, J=6.8 Hz, 3H), 1.01–1.35 (m, 2H). $^{13}$C NMR (90 MHz, DCl/$D_2$O) δ 174.2, 168.7, 168.2, 142.6, 133.4, 130.4, 129.3, 127.1, 114.7, 62.3, 59.4, 54.0, 47.4, 28.0, 24.0, 15.1. HRMS-CI calcd for $C_{18}H_{22}N_2O_5$ (M+H$^+$) 347.1528 found 347.1598. Anal. Calcd for $C_{18}H_{22}N_2O_5$: C, 62.42; H, 6.40; N, 8.09. Found: C, 62.46; H, 6.41 N, 8.02.

Example 4

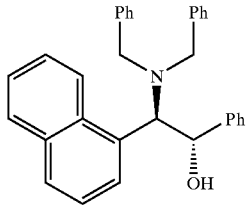

1-Naphthylboronic acid (110 mg, 0.64 mmol) and (S)-5-phenyl-2,2-dimethyl-4-hydroxy-1,3-dioxolane (130 mg, 0.67 mmol) were dissolved in ethanol (5 mL). To this solution was added dibenzylamine (126 mg, 0.64 mmol), the reaction was purged with nitrogen, sealed and stirred at room temperature for 24 hours. After the removal of volatiles, the residue was dissolved in ethylacetate (100 mL) and extracted with 3 N NaOH (3×50 mL) to remove unreacted boronic acid. Organic phase was dried over sodium sulfate and evaporated. The residue was chromatographed on silica gel using hexanes-ethylacetate (8:2) to yield pure product as a white foamy powder (238 mg; 84% yield, >99% de and >99%ee). [α]$_D$=+41° (c=0.14, $CH_3OH$); IR (KBr) δ 3061, 2923, 1599, 1493, 1452, 1278, 1124, 1026, 965, 799, 781, 768 cm$^{-1}$. $^1$H NMR (360 MHz, CD$_3$OD) δ 6.85–7.98 (m, 22H), 5.55 (d, J=9.2 Hz, 1H), 4.97 (d, J=9.2 Hz, 1H), 3.85 (d, J=14.2 Hz, 2H), 3.12 (d, J=14.2 Hz, 2H). $^{13}$C NMR (90 MHz, CD$_3$OD) δ 145.3, 141.1, 135.9, 135.4, 134.7, 129.9, 129.6, 129.2, 129.1, 128.9, 128.7, 128.6, 127.8, 127.3, 126.3, 125.9, 125.7, 75.8, 63.1, 55.4. HRMS-EI calcd. for C$_{32}$H$_{30}$NO (M+H$^+$) 444.2249, found 444.2285.

Example 5

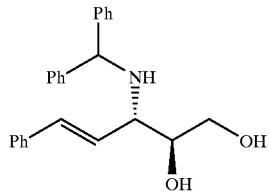

(R)-Glyceraldehyde (520 mg, ca. 75% in water, ca. 4.33 mmol) was dissolved in EtOH (15 mL) and to this solution was added aminodiphenylmethane (793 mg, 4.33 mmol), followed by (E)-2-phenylethenyl boronic acid (652 mg, 4.4 mmol). The reaction flask was sealed with plastic stopper and reaction mixture was vigorously stirred for 24 hours at ambient temperature. After the removal of volatiles, the residue was suspended in 6 N hydrochloric acid (20 mL) and heated with vigorous stirring at 60 C for 1 hour. After that time, the solution was cooled and filtered. The precipitate on the filter was washed with cold water (2×10 mL), ethylacetate (3×20 mL) and dried. Obtained 1201 mg of pure product (77% yield, >99%de, >99%ee). $^1$H NMR (250 MHz, CD$_3$OD) δ 7.30–7.65 (m, 15H), 6.60 (d, J=16 Hz, 1H), 6.33 (dd, J=16 Hz, 8.5 Hz, 1H), 5.59 (s, 1H), 4.18 (m, 1H), 3.93 (dd, J=8.5 Hz, 3.0 Hz, 1H), 3.57 (dd, J=10.9 Hz, 5.6 Hz, 1H), 3.40 (dd, J=10.9 Hz, 7.6 Hz, 1H). $^{13}$C NMR (63 MHz, C$_6$D$_6$) δ 144.8, 143.3, 137.1, 134.0, 129.0, 128.8, 128.7, 128.1, 127.9, 127.7, 127.4, 127.3, 126.8, 74.2, 65.2, 64.0, 61.5. HRMS-CI calcd. for C$_{24}$H$_{25}$NO$_2$ (M+H$^+$) 360.1885, found 360.1949.

The stereochemistry of the product was established as shown below:

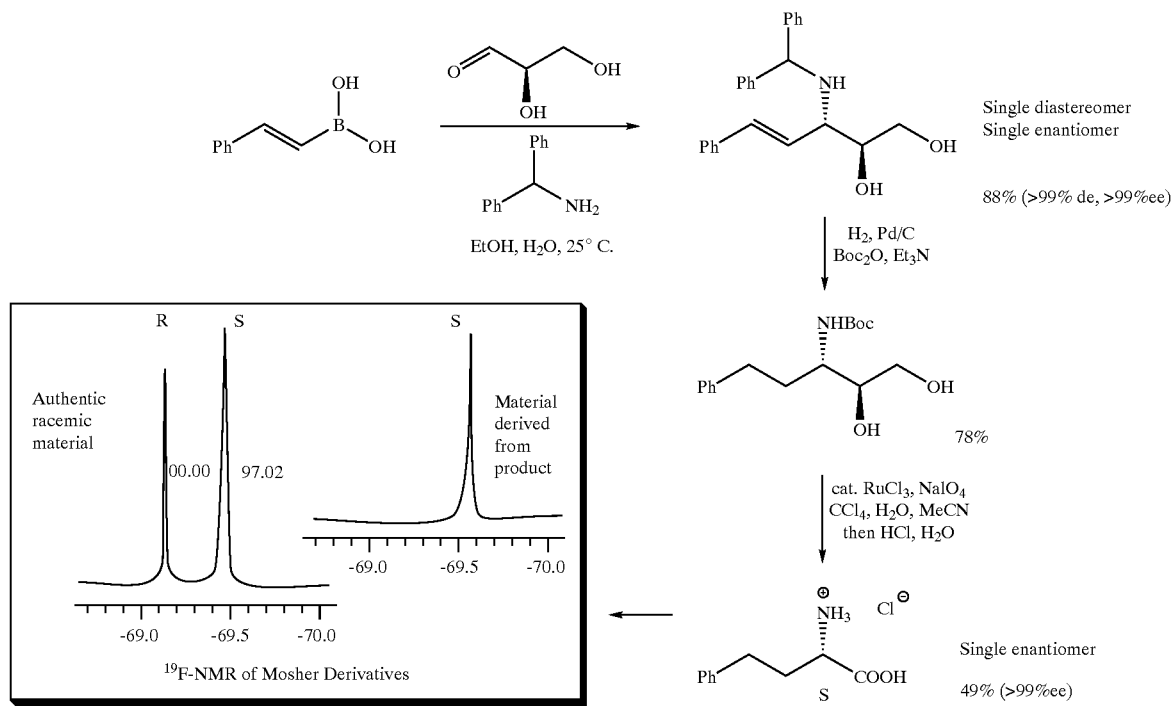

Example 6

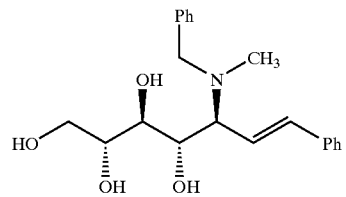

(D)-Ribose (158 mg, 1.05 mmol) was dissolved in EtOH (10 mL) and to this solution was added N-benzylmethylamine (127 mg, 1.05 mmol), followed by (E)-2-phenylethenyl boronic acid (163 mg, 1.1 mmol). The reaction flask was sealed with a plastic stopper and the reaction mixture was vigorously stirred for 24 hours at ambient temperature. After the removal of volatiles, the residue was redissolved in dichloromethane and purified by flash chromatography on silicagel using dichloromethane-methanol (600:50) as the eluent to obtain 278 mg of pure product (74% yield, >99%de). $^1$H NMR (360 MHz, CD$_3$OD). δ 7.20–7.45 (m, 10H), 6.61 (d, J=16.0 Hz, 1H), 6.33 (dd, J=16.0 Hz, 9.8 Hz, 1H), 3.98 (t, J=8.5 Hz, 1H), 3.65–3.88 (m, 5H), 3.58 (d, J=13.2 Hz, 1H), 3.49 (t, J=8.8 Hz, 1H), 2.25 (s, 3H). $^{13}$C NMR (90 MHz, CD$_3$OD) δ 138.9, 138.0, 137.8, 130.5, 129.6, 129.5, 128.8, 128.6, 127.6, 124.3, 77.2, 75.4, 71.4, 70.8, 64.1, 60.1, 37.9. HRMS-CI calcd. for $C_{21}H_{27}NO_4$ (M+H$^+$) 358.1940, found 358.1987.

Example 7

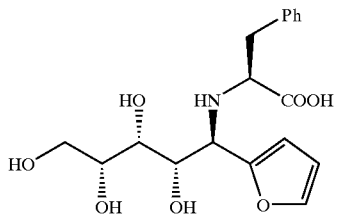

Prepared from (D)-xylose as in example 6 except that 2-furyl boronic acid and phenylalanine were used and the reaction was run for 48 hours in MeOH in 67% yield, >99% de, >99%ee. $^1$H NMR (360 MHz, CD$_3$OD) δ 7.55–7.60 (br, 1H), 7.21–7.38 (m, 5H), 6.43 (br, 2H), 4.27 (m, 1H), 4.05 (m, 1H), 3.50–3.75 (m, 6H), 3.15 (m, 1H). $^{13}$C NMR (90 MHz, CD$_3$OD) δ 173.0, 145.3, 137.6, 130.6, 130.4, 130.0, 128.4, 113.5, 111.9, 72.9, 72.5, 71.6, 64.0, 63.0, 59.9, 37.0. HRMS-CI calcd. for $C_{18}H_{23}NO_7$ (M+H$^+$) 366.1474, found 366.1553.

Example 8

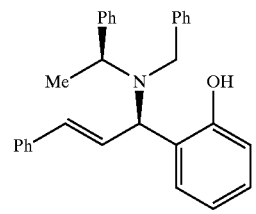

To the solution of salicylaldehyde (122 mg, 1 mmol) in ethyl alcohol (7 mL) was added (S)-N-benzyl-1-phenylethylamine (211 mg, 1 mmol), followed by (E)-2-phenylethenyl boronic acid (148 mg, 1 mmol). The reaction flask was purged with argon, sealed and stirred vigorously for 24 hours at ambient temperature. After the evaporation of volatiles, the product was isolated by flash column chromatography on silicagel using ethylacetate-hexanes (2:8) as the eluent (315 mg, 75% yield, >99%de, >99%ee).

Example 9

The high degree of stereocontrol of this process of the invention is illustrated in the following example. Thus, the final amino alcohol was subjected to Mosher amide analysis, which indicated a single enantiomer:

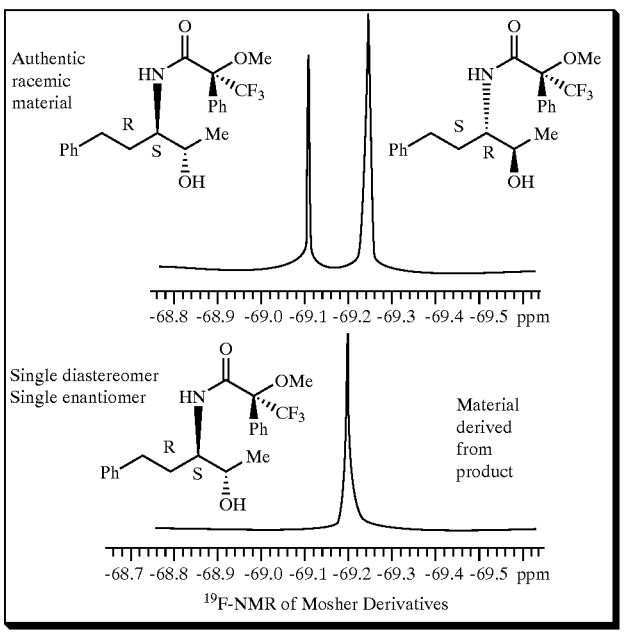

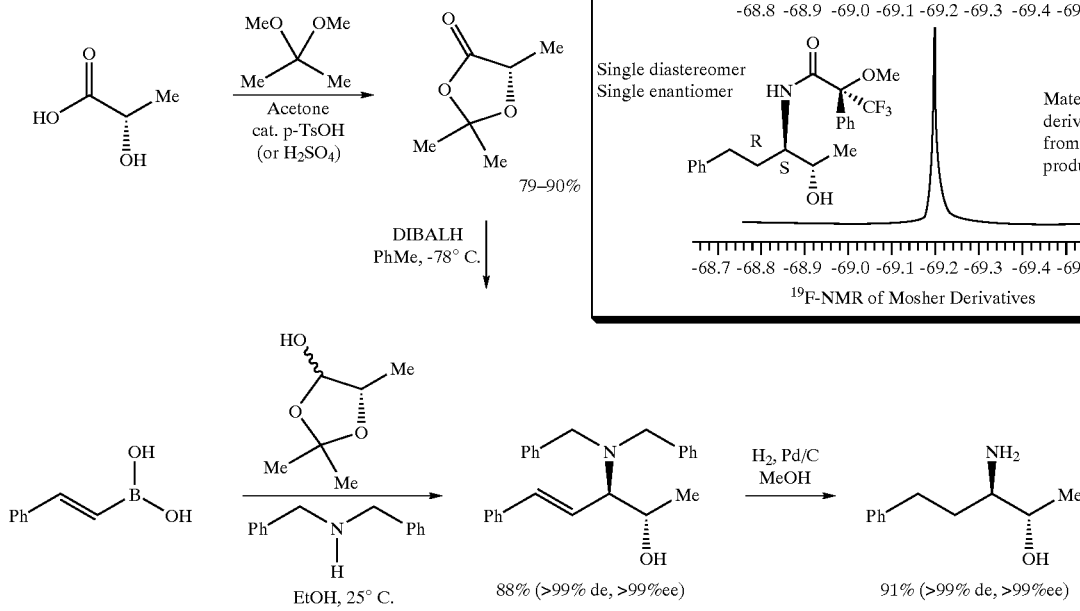

Some additional examples are shown in Table 1.

TABLE 1

Reactions with disaccharides

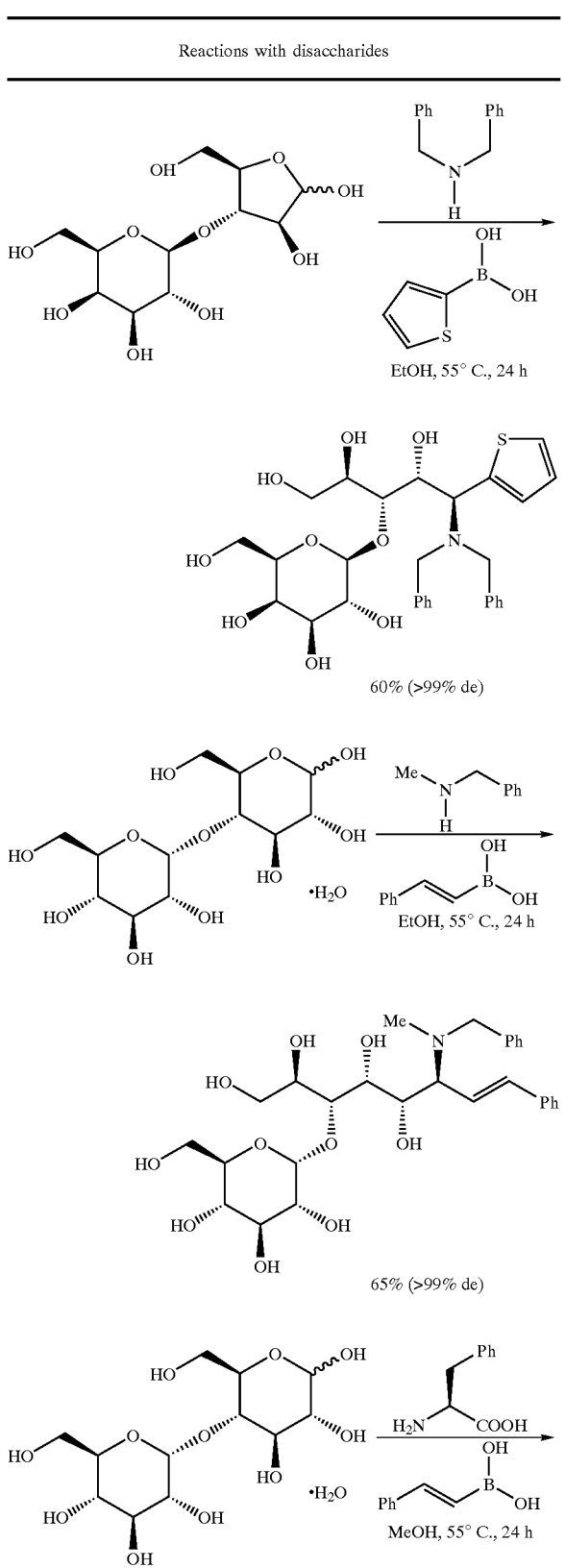

TABLE 1-continued

Reactions with disaccharides

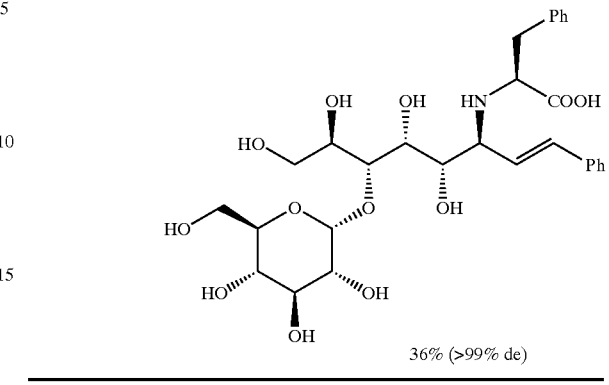

What is claimed:

1. A process for preparing a chiral reagent or catalyst comprising:
    reacting a metal or metalloid compound with one or more chiral ligands including an amino alcohol, wherein the metal or metalloid compound is reacted with the amino alcohol concurrent with synthesis of the amino alcohol.

2. A process for preparing a chiral reagent or catalyst comprising:
    mixing:
        a) an organoboronic acid;
        b) an amine; and
        c) a compound selected from the group consisting of an alpha-hydroxy aldehyde and a carbohydrate under conditions sufficient to form a chiral amino alcohol in one step; and
        c) a compound selected from the group consisting of an alpha-hydroxy aldehyde and a carbohydrate under conditions sufficient to form a chiral amino alcohol in one step; and
    reacting a metal or metalloid compound with one or more chiral amino ligands, the chiral amino alcohol being one of the one or more chiral amino ligands.

3. The process according to claim 2, wherein the metal or metalloid compound is reacted with the chiral amino alcohol concurrent with the synthesis of the chiral amino alcohol.

4. The process according to claim 2, wherein the metal or metalloid compound contains a metal or metalloid selected from the group consisting of B, Li, Mg, Al, Ti, V, Cr, Mn, Fe, Co, Ni, Cu, Zn, Zr, Mo, Ru, Rh, Pd, Ag, Re, Os, Ir, Pt, La, Ce and Yb; and
    the metal or metalloid compound reacts with the chiral amino alcohol to form one or more bonds between the metal and a heteroatom of the chiral amino alcohol.

5. The process according to claim 2 wherein at least one of the organoboronic acid, the amine, and the alpha-hydroxy aldehyde or carbohydrate, is attached to a solid support.

6. A process for preparing a chiral reagent or catalyst comprising:
    mixing:
        a) an organoboronic acid;
        b) an amine; and
        c) an aldehyde under conditions sufficient to form a chiral amine in one step; and
    reacting a metal or metalloid compound with one or more chiral amino ligands, the chiral amine being one of the one or more chiral amino ligands.

7. The process according to claim 6 wherein the amino ligand is further modified prior to reaction with the metal or metalloid compound.

8. The process according to claim 6, wherein the metal or metalloid compound contains a metal or metalloid selected from the group consisting of B, Li, Mg, Al, Ti, V, Cr, Mn, Fe, Co, Ni, Cu, Zn, Zr, Mo, Ru, Rh, Pd, Ag, Re, Os, Ir, Pt, La, Ce and Yb; and the metal or metalloid compound reacts with the chiral amine to form one or more bonds between the metal and a heteroatom of the chiral amine.

9. The process according to claim 6, wherein the metal or metalloid compound is reacted with the chiral amine concurrent with the synthesis of the chiral amine.

10. The process according to claim 6 wherein at least one of the organoboronic acid, the amine, and the aldehyde is attached to a solid support.

11. A process for preparing a chiral reagent or catalyst comprising:

mixing an organoboronic acid, an amine, and a carbonyl compound under conditions sufficient to form in one step a chiral amine selected from the group consisting of:

wherein $R^1$–$R^5$ and $R^8$–$R^{13}$ are independently selected from the group consisting of: hydrogen, alkyl, cycloalkyl, allyl, aryl, heteroaryl, alkenyl, allenyl, alkynyl, hydroxy, alkoxy, aryloxy, heteroaryloxy, acyl, carboxy, amino, alkylamino, dialkylamino, hydroxyamino, alkoxyamino, acylamino, carboxamido, alkylthio, arylthio, acylthio, trialkylsilyl, aryldialkylsilyl, diarylalkylsilyl, triarylsilyl, phosphinyl, alkylsulfonyl and arylsulfonyl, and derivatives thereof, or two or more of $R^1$–$R^5$ and $R^8$–$R^{13}$ taken together form a bridge of 2 to 20 atoms; and reacting a metal or metalloid compound with one or more chiral amino ligands, the chiral amine being one of the one or more chiral amino ligands.

12. The process according to claim 11, wherein the metal or metalloid compound contains a metal or metalloid selected from the group consisting of B, Li, Mg, Al, Ti, V, Cr, Mn, Fe, Co, Ni, Cu, Zn, Zr, Mo, Ru, Rh, Pd, Ag, Re, Os, Ir, Pt, La, Ce and Yb; and the metal or metalloid compound reacts with the chiral amine to form one or more bonds between the metal and a heteroatom of the chiral amine.

13. The process according to claim 11, wherein the metal or metalloid compound is reacted with one or more of the chiral amino ligands concurrent with the synthesis of the chiral amine.

14. A process for preparing a chiral reagent or catalyst comprising:

mixing:
a) an organoboronic acid;
b) an amine; and
c) a compound selected from the group consisting of an alpha-keto acid and glyoxylic acid under conditions sufficient to form a chiral amino acid in one step; and reacting a metal or metalloid compound with one or more chiral amino ligands, the chiral amino acid being one of the one or more chiral amino ligands.

15. The process according to claim 14, wherein the metal or metalloid compound contains a metal or metalloid selected from the group consisting of B, Li, Mg, Al, Ti, V, Cr, Mn, Fe, Co, Ni, Cu, Zn, Zr, Mo, Ru, Rh, Pd, Ag, Re, Os, Ir, Pt, La, Ce and Yb; and the metal or metalloid compound reacts with the chiral amino acid to form one or more bonds between the metal and a heteroatom of the chiral amino acid.

16. The process according to claim 14, wherein the metal or metalloid compound is reacted with the chiral amino acid concurrent with the synthesis of the chiral amino acid.

* * * * *